United States Patent [19]

Egger

[11] Patent Number: 5,581,240

[45] Date of Patent: Dec. 3, 1996

[54] PROCESS AND SYSTEM FOR CONTROLLING A WINDSHIELD WIPER, PARTICULARY FOR A MOTOR VEHICLE

[75] Inventor: Armin Egger, Bad Homburg, Germany

[73] Assignee: VDO Adolf Schindling AG, Frankfurt, Germany

[21] Appl. No.: 440,192

[22] Filed: May 12, 1995

[30] Foreign Application Priority Data

May 18, 1994 [DE] Germany .................... 44 17 436.5

[51] Int. Cl.$^6$ .................................................. G08B 21/00
[52] U.S. Cl. .................. 340/602; 340/601; 340/438; 340/439; 318/483; 318/DIG. 2; 318/444
[58] Field of Search .................... 318/443, 444, 318/483, DIG. 2; 388/907; 340/438, 439, 601, 602; 15/250 C, 250.13, 250.17

[56] References Cited

U.S. PATENT DOCUMENTS

| | | | |
|---|---|---|---|
| 4,740,735 | 4/1988 | Hayashi | 318/483 |
| 5,140,233 | 8/1992 | Wallrafen | 318/483 |
| 5,216,341 | 6/1993 | Nomura et al. | 318/444 |
| 5,306,992 | 4/1994 | Droge | 318/444 |
| 5,436,541 | 7/1995 | Mangler et al. | 318/483 |
| 5,453,670 | 9/1995 | Schaefer | 318/DIG. 2 |

*Primary Examiner*—Jeffery Hofsass
*Assistant Examiner*—Van T. Trieu
*Attorney, Agent, or Firm*—Martin A. Farber

[57] ABSTRACT

A process and a system for controlling a windshield wiper, in particular on a motor vehicle, in which a rain sensor is located on the glass to be wiped and within the region of the windshield wiper. The sensor outputs a sensor signal as a function of the amount of moisture. The signal is detected periodically and, when a reference degree of moisture is reached during a measurement cycle, the system produces a triggering signal and the windshield wiper is activated. The wiping process takes place even when the windshield wiper is wetted with moisture only to a slight but nevertheless disturbing extent. In the process, when a degree of moisture below a reference degree of moisture is present at the end of the measurement cycle, this degree of moisture is included additively to the degree of moisture of a further measurement cycle. Thereupon, the degree of moisture of the further measurement cycle is compared with the reference degree of moisture.

12 Claims, 3 Drawing Sheets

PROCESS AND SYSTEM FOR CONTROLLING A WINDSHIELD WIPER, PARTICULARY FOR A MOTOR VEHICLE

FIELD AND BACKGROUND OF THE INVENTION

The present invention relates to a process and system for controlling a windshield wiper, particularly on a motor vehicle, wherein a rain sensor is located on the windshield to be wiped and in the region of the windshield wiper to give off a sensor signal as a function of the amount of moisture. The sensor signal is detected cyclically and, when a given degree of moisture is reached in a measurement cycle, the system produces a triggering signal and controls the windshield wiper.

Means for controlling windshield wipers are known in which the amount of moisture on the windshield is detected by sensors arranged on the windshield.

When a predetermined amount of moisture is reached on the windshield, the windshield wiper motor is automatically turned on. For optimal vision, it is, however, important to adapt the operation of the windshield wiper to the prevailing intensity of the rain, which can be effected by connection and disconnection, change of the interval between individual wiping processes, change of the speed and/or switching between intermittent operation (individual wipe) or continuous operation (continuous wiping).

In known processes, a trigger signal for the windshield wiper is given off depending on whether the sensor signal has reached or exceeded a predetermined threshold value. In this case, the threshold value represents the transition from a wet to a dry windshield. In the case of a fine rain or mist, the windshield wiper of the vehicle is covered with moisture, but this threshold value is not exceeded in view of the fact that the amplitude of the signal is not changed substantially. The windshield wiper signal is not given off.

Optical vision on the part of the driver of the vehicle, however, requires actuation of the windshield wiper.

SUMMARY OF THE INVENTION

It is an object of the invention to provide a process and a system for control of a windshield wiper in which the wiping is effected even when the windshield wiper is wetted with moisture only to a slight but nevertheless disturbing extent.

According to the invention, in the event of a degree of moisture below the reference degree of moisture ($S_{ref}$) within a measurement cycle, this degree of moisture is included, increasing it, in the degree of moisture of another measurement cycle, and the degree of moisture of the other measurement cycle is compared with the reference degree of moisture ($S_{ref}$).

The advantage of the invention is that even moisture of the windshield which does not cause any sudden change in the sensor signal, because it is of too small an amount, is also taken into account for the control of the windshield wiper. This is effected in the manner that the moisture which has already impinged on the windshield are also included in the new measurement process. In this way, individual automatic control of the windshield wiper, for instance in the event of a drizzle, is possible without the driver having to turn on the windshield wiper on manually.

The new starting value is advantageously formed as a function of the amount of moisture determined in the preceding measurement cycle.

The new starting value can, in this connection, represent a percentage of the amount of moisture previously measured.

The new starting value is formed only when a predetermined period of time has exceeded, such that drying of the amount of moisture has not taken place.

According to a feature of the invention, the degree of moisture forms the starting value of a further measurement cycle.

Further according to the invention, the starting value is formed as a function of the degree of moisture.

Also, the invention provides that the starting value is derived as percentage of the degree of moisture.

Further, the degree of moisture is represented by the instantaneous sensor signal ($S_m$).

Still further according to the invention, the degree of moisture is represented by the sum ($S_n$) of the changes in moisture ($\Delta S_n$).

Yet further, the starting value is only formed after a delay time ($t_z$) has been exceeded.

In a further development of the invention, when there is a degree of moisture below the reference degree of moisture ($S_{ref}$) at the end of a measurement cycle, a triggering signal is produced when the degree of moisture is present for a given period of time ($t_t$).

According to another feature of the invention, the windshield wiper is started when the degree of moisture in a measurement cycle at the end of the delay time ($t_t$) contains a part of the reference degree of moisture ($S_{ref}$).

The invention also provides the feature that the degree of moisture is represented by the sum ($S_m$) of the changes in moisture.

One advantageous embodiment for the carrying out of the process provides that the sensor is connected via an analog/digital converter (4) to a microcomputer (5) and that a program in accordance with the process of the invention is provided for the microcomputer (5).

In this case, the sensor is preferably a resistive moisture sensor (1).

The invention permits numerous embodiments. One of them will be explained in further detail with reference to the figures shown in the drawing.

BRIEF DESCRIPTION OF THE DRAWINGS

With the above and other objects and advantages in view, the present invention will become more clearly understood in connection with a detailed description of preferred embodiments, when considered with the accompanying drawing, of which.

DETAILED DESCRIPTION OF THE PREFERRED EMBODIMENTS

Figure 1:
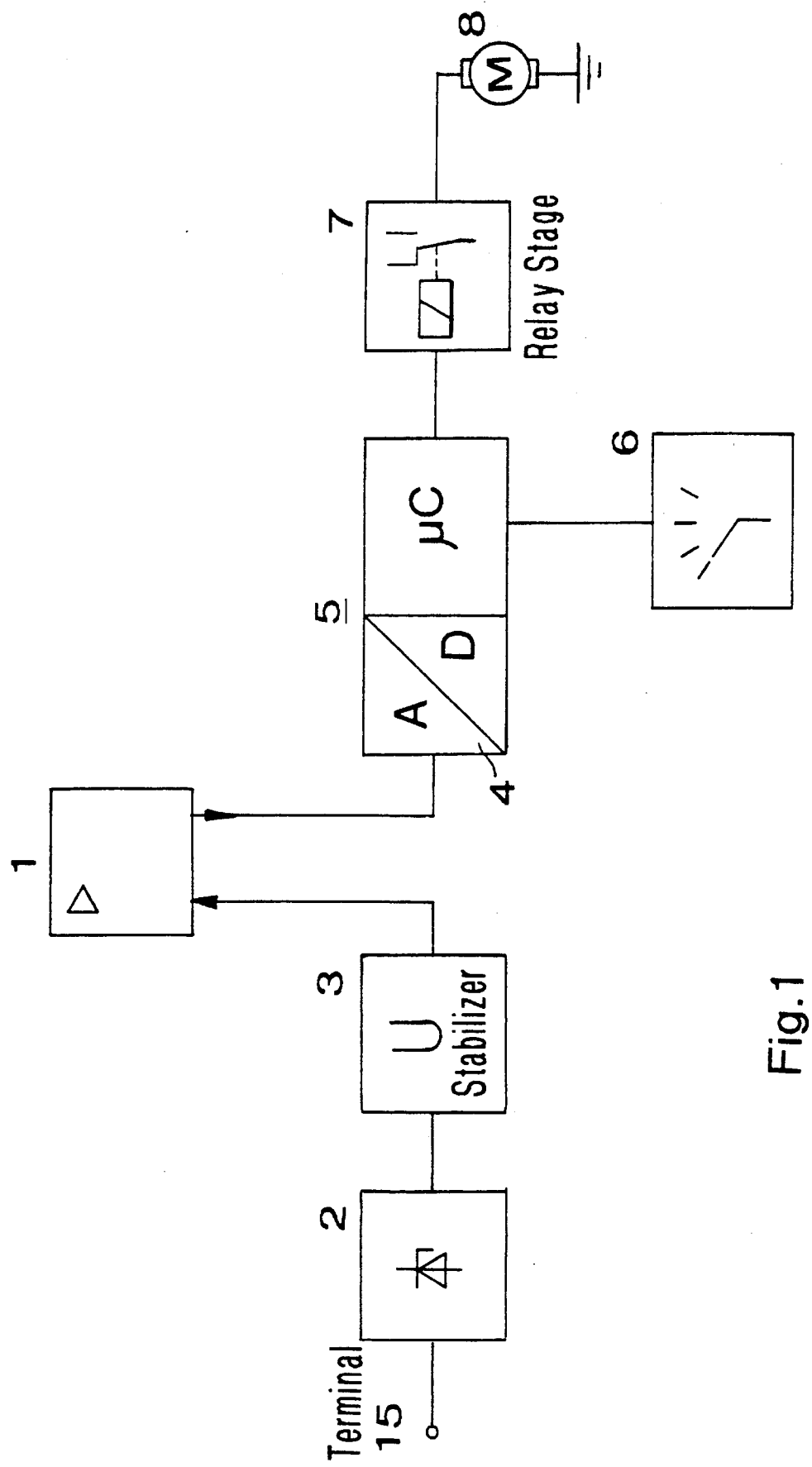
FIG. 1 is a block diagram of a system for the carrying out of the process of the invention.

In the device shown in FIG. 1, the degree of wetting of the windshield is determined by means of a resistive sensor 1 to which operating voltage is fed via the terminal 15 of the car's electrical system via a noise-voltage filter 2 and a stabilizing circuit 3. Resistive moisture sensors are known per se and need not be explained in detail for an understanding of the present invention. An amplifier is associated with the sensor 1 so that the output voltage of the sensor is fed directly to an analog/digital converter 4 of a microcomputer 5. The microcomputer 5 is connected to an operating switch 6 which is preferably developed as a steering column switch and has detent positions for continuous operation and automatic operation as well as momentary-contact position for a single wipe. The motor 8 of a windshield wiper is connected via a relay stage 7 to an output of the microcomputer 5. Included within the computer 5 is a timer (not shown) for timing steps of the process in FIG. 2. Specific events noted by the timer are shown in FIG. 3.

Figure 2:
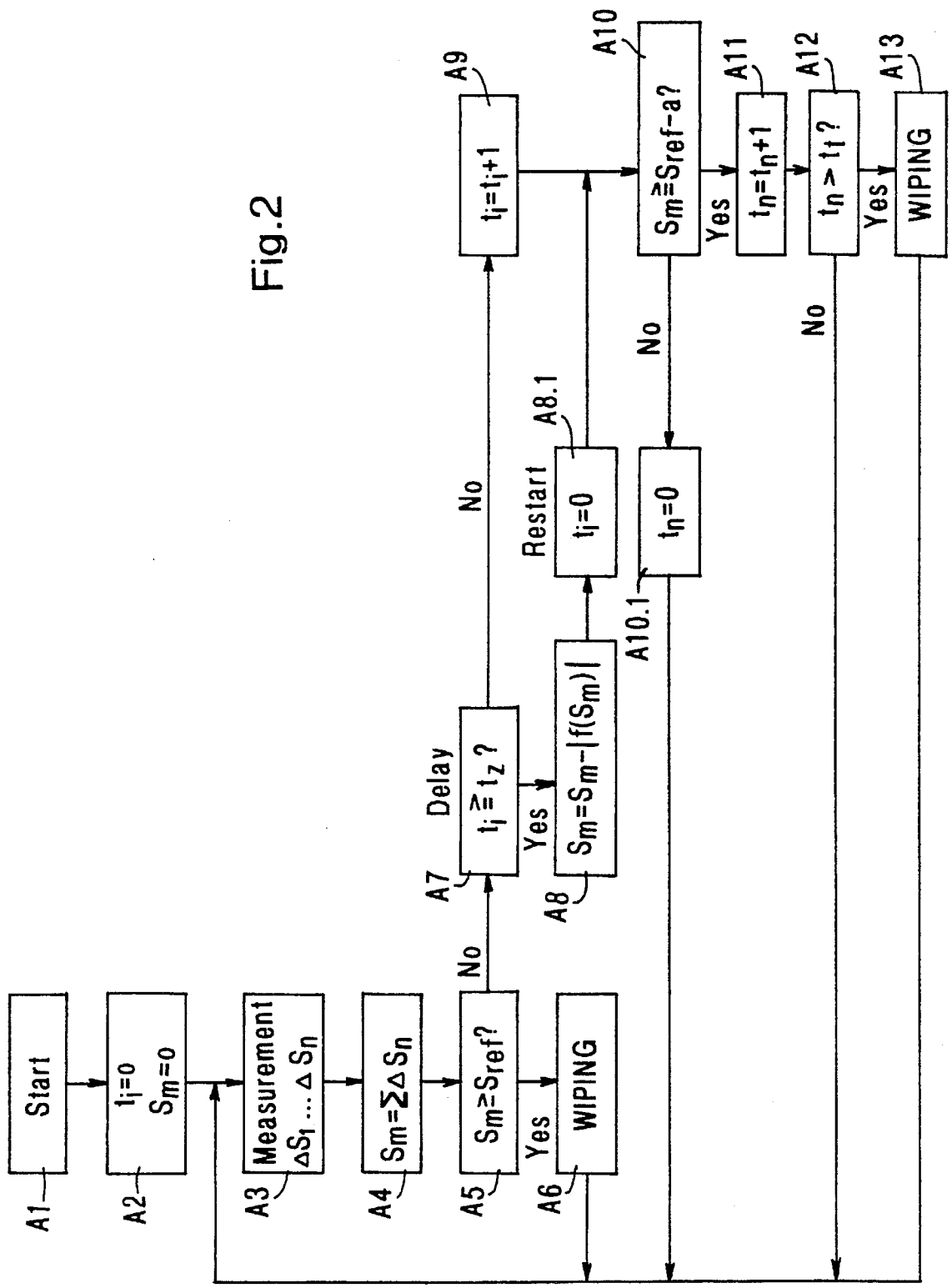
FIG. 2 is a flow chart of a program provided for the microcomputer in the system of FIG. 1.
Figure 3:
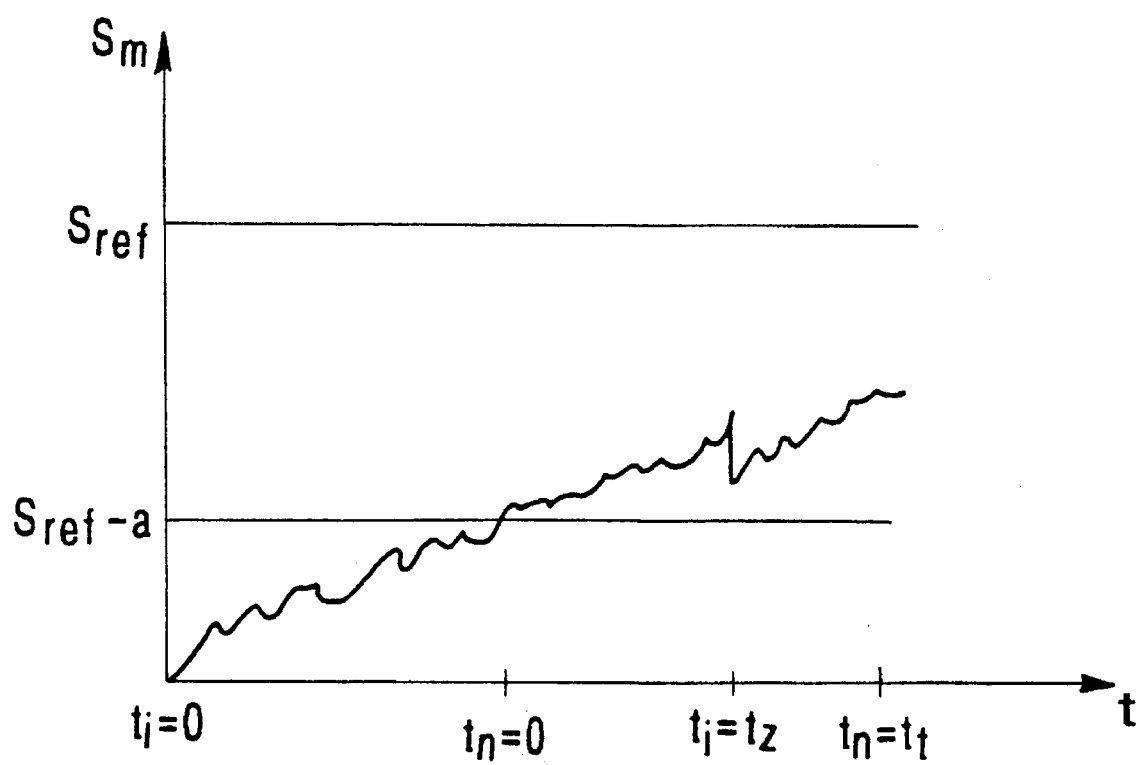
FIG. 3 is a time graph.

An ordinary method for the control of a windshield wiper is shown in FIG. 2 in steps A1 to A6. The process starts at A1 and, at step A2, the timer and the sum of sensor signal changes are reset to zero. In a succession of identical time intervals the changes in the amplitude of the sensor signal are measured and the corresponding changes in amplitude $\Delta S_1$ to $\Delta S_n$ are determined in step A3. These changes are summed at step A4.

At step A5, the sum of the amplitude changes $S_m$ is compared with the threshold value $S_{ref}$ representing the dry windshield. If this threshold value is exceeded upon an increase in the moisture on the windshield, the wiping is commenced at step A6, after which the process reverts to step A3. Sudden individual changes in the sensor signal which are caused by raindrops are in this way filtered out.

If the sum $S_m$ does not exceed the threshold value $S_{ref}$ at step A5, then, after a delay time $t_z$ at step A7, the value $S_m$ is determined in step A8. This is effected by deduction of an amount which is determined as a function of the sum formed from the measurement results. Thus, the newly determined value amounts to about 70% of the sum $S_m$ reached. However, it is also conceivable that the amount to be deducted is determined as a function of the instantaneous measure value $S_n$ and/or the sum $S_m$.

The value determined in this manner forms the starting value for a new measurement cycle which, accordingly, starts with a value other than zero upon resetting the timer at A8.1 to zero.

Alternatively, at step A7, prior to the delay time $t_z$, the process may advance via step A9 wherein the timer increments the time by one unit at step A9, after which the process continues with step A10.

In a further aspect of the invention, in order to detect a very slow decrease in amplitude of the sensor signal, it is checked at A10 whether the value $S_m$ formed on the basis of measurements is greater than a threshold value $S_{ref}$ reduced by a constant value a, shown also in FIG. 3. If so, then inquiry is made at later time, step A11, whether this reduced part of the sum is present for a given time $t_t$. If this time $t_t$ is exceeded at step A12, the wiping is started at step A13, even though the threshold value $S_{ref}$ has not been exceeded. Thereafter, the process reverts to step A3. In this way, optical disturbances in the field of view of the driver are eliminated, although no increase in moisture can be noted. The two processes described can also take place separately.

Alternatively, at step A10, for lower values of $S_m$,' the timer is reset to zero at step A10.1, and the process reverts to step A3.

I claim:

1. A method for controlling a windshield wiper, including a windshield wiper on a motor vehicle, comprising the steps of placing a rain sensor on a windshield in a region of the windshield to be wiped by a wiper, the sensor outputting a sensor signal as a function of an amount of moisture on the windshield;

detecting the sensor signal periodically during a succession of measurement cycles to provide a succession of detected sensor signals;

summing the sensor signals detected in each of the succession of measurement cycles, a sum of the detected sensor signals indicating a degree of moisture;

upon reaching a degree of moisture in a measurement cycle equal or greater than a reference degree of moisture, producing a triggering signal for controlling the windshield wiper;

upon occurrence of a degree of moisture below the reference degree of moisture within a measurement cycle which includes a present degree of moisture, establishing an initial degree of moisture equal to a fraction of the present degree of moisture;

summing the initial degree of moisture to the degree of moisture of a subsequent measurement cycle to obtain a summation of moisture degrees; and comparing the resulting summation of degree of moisture with the reference degree of moisture for producing a wiper triggering signal.

2. A method according to claim 1, wherein the summation of degree of moisture serves as a starting value of a further measurement cycle.

3. A method according to claim 2, wherein the starting value is formed as a function of the summation of degree of moisture.

4. A method according to claim 3, wherein the starting value is derived as a percentage of the summation of the degree of moisture.

5. A method according to claim 1, wherein the degree of moisture of a first measurement of a series of measurements is represented by the instantaneous sensor signal.

6. A method according to claim 1, wherein, after a plurality of measurements, the degree of moisture is represented by the sum of the increments in moisture.

7. A method according to claim 3, wherein the starting value is formed only after a delay time from a previous measurement has been exceeded.

8. A method for controlling a windshield wiper, including a windshield wiper on a motor vehicle, comprising the steps of:

placing a rain sensor on a windshield region of the windshield to be wiped by a wiper, the sensor outputting a sensor signal as a function of an amount of moisture on the windshield;

detecting the sensor signal periodically during a succession of measurement cycles to provide a succession of detected sensor signals;

summing the sensor signals detected in each of the succession of measurement cycles, a sum of the detected sensor signals indicating a degree of moisture;

upon reaching a degree of moisture in a measurement cycle equal or greater than a reference degree of moisture, producing a triggering signal for controlling the windshield wiper; and wherein, upon an occurrence of a degree of moisture below the reference degree of moisture at the end of a measurement cycle, producing a triggering signal upon the presence of the degree of moisture within a given interval of time.

9. A method according to claim 8, further comprising a step of starting the windshield wiper when the degree of moisture in a measurement cycle at the end of the given time interval is a part of the reference degree of moisture.

10. A method according to claim 9, wherein the degree of moisture is represented by the sum of increments in measurements of moisture.

11. A system for operating a windshield wiper, including a windshield wiper on a motor vehicle, comprising:

a sensor of intensity of rain located on a windshield in a region of the windshield to be wiped by the wiper, the sensor outputting a sensor signal as a function of an amount of moisture on the windshield;

a computer, and an analog/digital converter connecting said sensor to said computer; and wherein said computer is operative in accordance with a program providing a process comprising the steps of:

detecting the sensor signal periodically during a succession of measurement cycles to provide a succession of detected sensor signals;

summing the sensor signals detected in each of the succession of measurement cycles, a sum of the detected sensor signals indicating a degree of moisture;

upon reaching a degree of moisture in a measurement cycle equal or greater than a reference degree of moisture, producing a triggering signal for controlling the windshield wiper;

upon occurrence of a degree of moisture below the reference degree of moisture within a measurement cycle which includes a present degree of moisture, establishing an initial degree of moisture equal to a fraction of the present degree of moisture;

summing the initial degree of moisture to the degree of moisture of a subsequent measurement cycle to obtain a summation of moisture degrees; and comparing the resulting summation of degrees of moisture with the reference degree of moisture.

12. A system according to claim 11, wherein the sensor is a resistive moisture sensor.

* * * * *